US011745258B2

(12) United States Patent
Itofuji et al.

(10) Patent No.: US 11,745,258 B2
(45) Date of Patent: Sep. 5, 2023

(54) CASTING SOLIDIFICATION ANALYSIS METHOD, CASTING METHOD, AND ELECTRONIC PROGRAM

(71) Applicants: I2C Co., Ltd, Yamaguchi (JP); UBE STEEL CO., LTD., Yamaguchi (JP)

(72) Inventors: Haruki Itofuji, Yamaguchi (JP); Yutaka Miyamoto, Yamaguchi (JP)

(*) Notice: Subject to any disclaimer, the term of this patent is extended or adjusted under 35 U.S.C. 154(b) by 55 days.

(21) Appl. No.: 16/761,807

(22) PCT Filed: Apr. 25, 2018

(86) PCT No.: PCT/JP2018/016890
§ 371 (c)(1),
(2) Date: May 6, 2020

(87) PCT Pub. No.: WO2019/087435
PCT Pub. Date: May 9, 2019

(65) Prior Publication Data
US 2021/0178464 A1 Jun. 17, 2021

(30) Foreign Application Priority Data
Nov. 6, 2017 (JP) .............................. JP2017-213935

(51) Int. Cl.
| | | |
|---|---|---|
| B22D 46/00 | (2006.01) | |
| B22D 27/20 | (2006.01) | |
| C22C 1/10 | (2023.01) | |
| G01N 25/06 | (2006.01) | |
| G01N 33/205 | (2019.01) | |
| C21C 1/10 | (2006.01) | |

(52) U.S. Cl.
CPC ............. B22D 46/00 (2013.01); C21C 1/10 (2013.01); G01N 25/06 (2013.01); G01N 33/205 (2019.01)

(58) Field of Classification Search
CPC .......... B22D 27/20; B22D 46/00; C22C 1/10; G01N 25/04; G01N 25/06; G01N 33/205

USPC .................................................. 164/4.1, 457
See application file for complete search history.

(56) References Cited

U.S. PATENT DOCUMENTS 7,974,818 B2 * 7/2011 Sakurai et al. ........ B22D 46/00
703/2

FOREIGN PATENT DOCUMENTS

| CN | 1873401 A | * 12/2006 | ............. G01N 25/72 |
|---|---|---|---|
| CN | 1996319 A | * 7/2007 | ............. G06F 17/50 |
| JP | 07-209220 A | 8/1995 | |
| JP | 08-253803 A | 10/1996 | |
| JP | 10-296385 A | 11/1998 | |
| JP | 2008-188671 A | 8/2008 | |
| JP | 2010-125465 A | 6/2010 | |

OTHER PUBLICATIONS

Machine translation of CN 1873401 A (Year: 2006).*
Machine translation of CN 1996319 A (Year: 2007).*
ISR; Japan Patent Office; Tokyo; dated Jun. 5, 2018.
Chisamera, M. et al; Simultaneous Cooling and Contraction/ Expansion Curve Analysis During Ductile Iron Solidification, Apr. 2012.

* cited by examiner

Primary Examiner — Kevin P Kerns
(74) Attorney, Agent, or Firm — Patshegen IP; Moshe Pinchas

(57) ABSTRACT

A casting solidification analysis method, which can analyze positions of shrinkage cavities more accurately than in the past, a casting method using the above method, and an electronic program are provided. A following casting solidification analysis method is provided. An amount of expansion/shrinkage for each solidification step length separated by inflection points in a cooling curve is determined, by setting a solid phase ratio at a completion of pouring to 0, setting a solid phase ratio at an end of solidification to 1.0, and determining the expansion/shrinkage amount for the each solidification step length by proportionally distributing the each solidification step length to the total solid phase ratio length.

5 Claims, 14 Drawing Sheets

Critical points of volumetric change in solidification curve.

Casting design for test block. (Unit ; mm )

Temperature and time schedule for melting, liquid treatment and pouring.

Cooling curves during the solidification of test blocks.

Relationship between temperature and solidification ratio at each reaction of test blocks.

Amount of expansion / shrinkage at each reaction of test blocks.
a)Liquid shrinkage, b)Primary austenite shrinkage, c)Eutectic expansion, d)Between cell austenite shrinkage a) Shrinkage distribution at cross section of test blocks.
(The right side of the photos is the gate)

b) Filled Ratio 99.9~0.0% c) G/√R 0.7~0.0

Result of CAE analysis for test blocks.

a) Shrinkage distribution   b) Filled Ratio 99.9–0.0%

Cross section of Mc=10cm block and analysis result.

Solidification curve in test materials

Solidification ratio and amount of expansion/shrinkage for Mc=10cm block.

Critical Points of Volumetric Change in Solidification Curve

Casting design of Test material (1) Filled Ratio = 0~99.9%

(2) Shrinkage Distribution at Convex Sections of Actual material (3) Niyama Criteria = 0~1%

Results of CAE analysis in Sample Casting (a) <u>Mushy type solidification small-sized FCD</u>

(b) <u>Semi-mushy type solidification Thick and/or flat FCD</u>

CASTING SOLIDIFICATION ANALYSIS METHOD, CASTING METHOD, AND ELECTRONIC PROGRAM

TECHNICAL FIELD

The present invention relates a casting solidification analysis method, a casting method and an electronic program.

BACKGROUND ART

A large-sized spheroidal graphite cast iron casting (hereinafter referred to as large-sized SGI) can be soundly produced without shrinkage cavities by maximizing the expansion pressure and volume of eutectic graphite (Non-Patent Documents 1-4), even if the cast design is riserless. However, in the case of a plate casting, shrinkage cavities may occur under riserless conditions. Therefore, the riserless method is not applicable to all shapes. For this reason, in practice, a method has been employed, in which a riserless safety index is determined from a casting modulus (hereinafter, referred to as Mc) and a shape factor to determine whether or not the riserless method is applicable (Non-Patent Documents 5-7). If it is determined that a riser is needed, it is designed in the same manner as cast steel. There is also a report on a heat balancer method, which can handle small and medium-sized SGI with a thickness of 50 mm or less (Non-Patent Documents 8 and 9).

However, in the case of a large-sized SGI, as the casting shape becomes more complicated, it becomes more difficult to preliminarily determine the shrinkage cavities occurrence sites. If welding repairs are not possible in the quality specification, castings of several tens of tons may have to be reproduced. In order to avoid such a risk, an excessive method may be adopted, which may reduce the working efficiency and the yield. One of the factors is that it is difficult to predict the shrinkage cavities of SGI by CAE analysis. Typical prediction methods include a modified temperature gradient method, a temperature gradient method, a closed loop method, and the like, and an appropriate prediction method can be selected according to a material and a producing method (Non-Patent Document 10). However, these analytical precisions have been established for cast steel castings, aluminum alloy castings, and the like, which take on a solidified form that is constantly shrinking by skin-forming solidification.

Various analysis software has been developed for SGI castings with mushy type of solidification and graphite expansion (Non-Patent Documents 12-15).

PRIOR ART DOCUMENTS

Non-Patent Documents

Non-Patent Document 1: S. I. Kansay: Ductile Iron I-Production, Quebec Iron and Titanium (1992) 158-161
Non-Patent Document 2: Bakk Chang: Journal of Japanese Foundry Engineering Society 55 (1983) 113
Non-Patent Document 3: M. Taffazzoli, V. Kondic: Foundry Management and Technology, 104 (1976) 86
Non-Patent Document 4: H. Itofuji, K. Kawamura, N. Hashimoto and H. Yamada: AFS Trans. 98 (1990) 585-595
Non-Patent Document 5: Bakk Chang, Kiyoaki Akechi, Kenzo Hanawa: Spheroidal cast iron—Basics, theory and application (AGNE) (1983)
Non-Patent Document 6: Toshiki Yoshida, Kentaro Yano, Masahide Kawabata: Journal of Japan Foundry Engineering Society 71 (1999) 104
Non-Patent Document 7: T. Kotani, K. Edane, K. Iwakado and H. Itofuji: Gastech (2016)
Non-Patent Document 8: H. Itofuji, M. Tamura, H. Ito, T. Nishimura and Y. Esashika: Mater. Trans. 51 (2010) 103
Non-Patent Document 9: K. Ishikawa, T. Kotani, t. Ogino and H. Itofuji: The 12 AFC (2013)
Non-Patent Document 10: E. Niyama, T. Uchida, M. Morikawa and S. Saito: AFS International Cast Metal Journal 7 (1982) 52
Non-Patent Document 11: Naotaka Deki: Journal of Japan Foundry Engineering Society 86 (2014) 914
Non-Patent Document 12: Takayuki Tashiro: Journal of Japan Foundry Engineering Society 86 (2014) 922
Non-Patent Document 13: Atsushi Murakami, Masahiko Takishita: Journal of Japan Foundry Engineering Society 86 (2014) 931
Non-Patent Document 14: Takeshi Yonezawa: Journal of Japan Foundry Engineering Society 86 ((2014) 940
Non-Patent Document 15: Isamu Takahashi, Toshio Uchida, Kouichi Anzai: Journal of Japan Foundry Engineering Society 78 (2006) 661
Non-patent Document 16: Eisuke Niiyama, Kouichi Anzai: Journal of Japanese Foundry Engineering Society 67 (1995) 30

DISCLOSURE OF THE INVENTION

Problems to be Solved by the Invention

Various analysis software has been developed for SGI castings with mushy type of solidification and graphite expansion, but the accuracy is currently low (Non-Patent Documents 11-14).

An object of the present invention is to provide a casting solidification analysis method with high prediction accuracy.

Solutions for Solve the Problems

In order to improve the prediction accuracy, it is necessary to use analysis software, which takes into account the solidification morphology unique to SGI.

In the present invention, a shrinkage cavities prediction method was investigated. The shrinkage cavities prediction method is as follows. A theoretical volume of shrinkage/expansion associated with solidification is calculated, and is substituted into the zone where the cooling curve is separated at inflection points.

The invention according to certain embodiments is a casting solidification analysis method, wherein an amount of expansion/shrinkage for each solidification step length separated by inflection points in a cooling curve is determined, by setting a solid phase ratio at a completion of pouring to 0, setting a solid phase ratio at an end of solidification to 1.0, and determining the expansion/shrinkage amount for the each solidification step length by proportionally distributing the each solidification step length to the total solid phase ratio length.

The invention according to certain embodiments is the casting solidification analysis method according to the previous paragraph, wherein a cast product is a thick cast product having a thick part of 50 mm or more, or a cast product with modulus Mc (volume V/surface area S) of 2.5 cm or more.

The invention according to certain embodiments is the casting solidification analysis method according to the previous paragraphs, wherein the casting is a spheroidal graphite cast iron casting.

The invention according to certain embodiments is a casting method for performing casting based on the result of analysis by the casting solidification analysis method according to any of the previous paragraphs.

The invention according to other embodiments is an electronic program comprised from; a step, in which inflection points are determined from the cooling curve by a tangent method or a differential curve, and each solidification step length separated by the inflection points is determined; and a step, in which a solid phase ratio at a completion of pouring is set to 0, a sold phase ratio at an end of solidification is set to 1.0, and an expansion/shrinkage amount for the each solidification step length is determined by proportionally distributing the each solidification step length to the total solid phase ratio length.

The invention according to other embodiments is a solidification analysis method, which analyses shrinkage and expansion temperatures at an early stage of solidification and shrinkage temperature at an end of solidification by connecting a latent heat pattern released during solidification by a straight line from solid phase ratio 0 to 1.0.

Effects of the Invention

In the present invention, the following procedure is basically used.

1. The inflection points on the cooling curve are determined.
2. The inflection points indicate changes in solidification progress.
3. The changes are that during the solidification process, some structures expand and others shrink.
4. Therefore, the expansion/shrinkage amount is given by the following procedure.

And, in the present invention, the expansion/shrinkage amount is taken as a function of the solid phase ratio in this procedure. The solid phase ratio is such that the solid phase ratio is set to 0 when casting is completed and set to 1.0 when solidification is completed.

5. The each solidification step length is proportionally distributed to the total solid phase ratio length.

The expansion/shrinkage amount is given to each solidification step length.

Conventionally, the calculation of the initial amount of liquid shrinkage has been started from the casting (ladle) temperature.

On the other hand, the present invention is also different from the related art in that the temperature in the mold after the casting is completed, that is, the filling completion temperature is started.

With such a configuration, in order to improve the prediction accuracy, an analysis is performed in consideration of the solidification morphology peculiar to the SGI, and the theoretical volume of shrinkage/expansion accompanying solidification is obtained. A remarkable effect that the prediction accuracy can be increased can be achieved by using a shrinkage cavities prediction method, in which the values are substituted into the applied zones separated by the inflection points of the cooling curve and calculated.

MODE FOR CARRYING OUT THE INVENTION

Example

Example of the present invention is shown below.

(Shrinkage Cavities Analysis)

Figure 1:
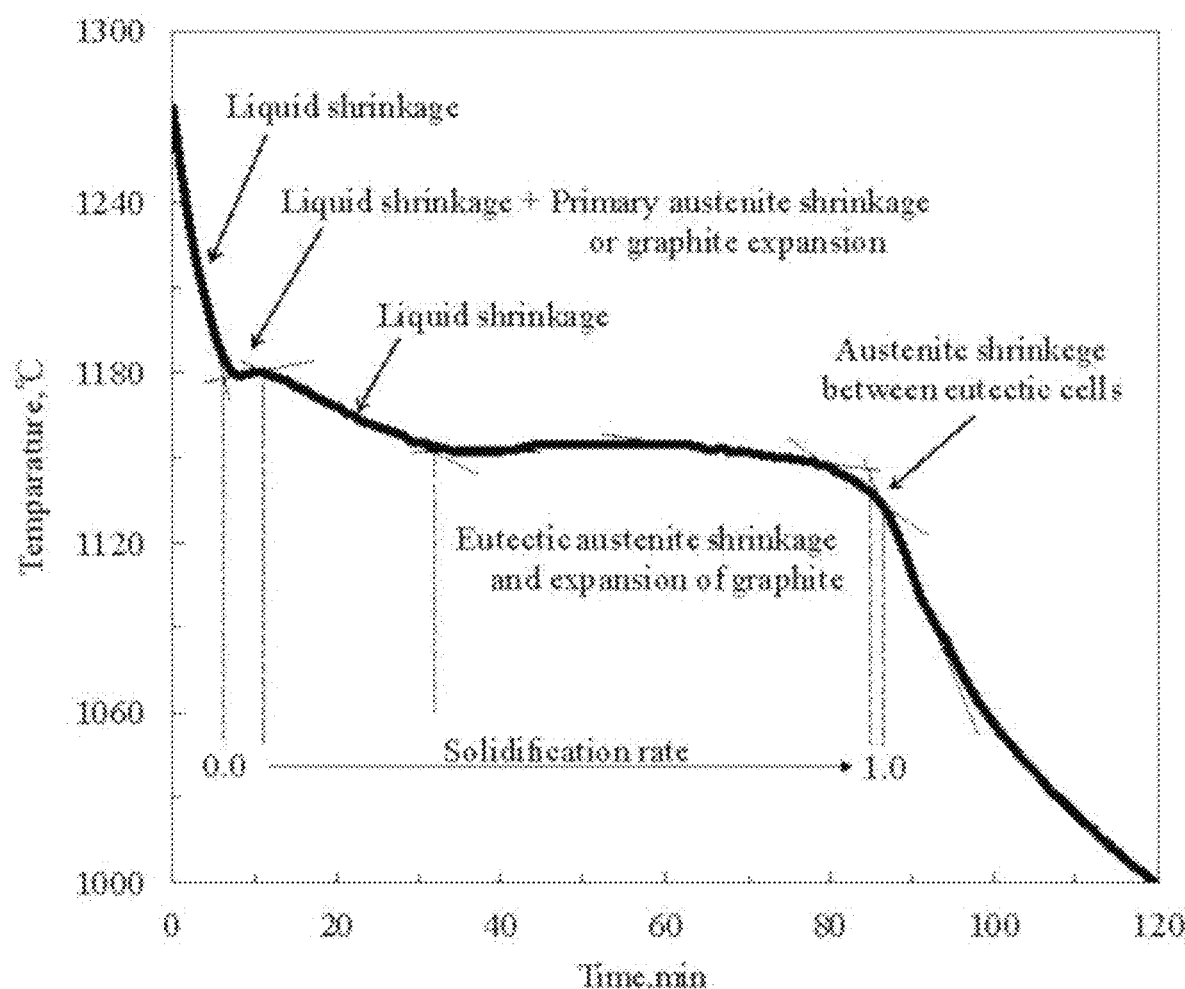
FIG. 1 shows a graph indicating inflection points in a cooling curve.

In order to predict shrinkage cavities by reproducing the expansion/shrinkage behavior occurring during coagulation by coagulation analysis, we first quantified the volume change treated as an input value. Until solidification was completed, (a) a temperature of each reaction and a solid phase ratio at that time, and (b) a theoretical volume change were calculated (Non-Patent Document 5). In (a), the inflection points were determined by a tangent method from the actually measured cooling curve. FIG. 1 shows an occurrence image of each reaction in the cooling curve. The solid phase ratio was started at the time of completion of casting, and each reaction was in turn liquid shrinkage, primary crystal reaction, eutectic reaction, and finally shrinkage of austenite between eutectic cells. (b) was obtained by the equation (1) using the C and Si amounts of the chemical composition and the casting completion temperature.

$$TV = Sl + Epg (\text{or } Sp\gamma) + Eeg + Se\gamma \qquad (1)$$

TV=Amount of volume change (vol. %)
Sl=Amount of liquid shrinkage (vol. %)
Epg=Amount of expansion due to primary graphite (vol. %)
Sp γ=Shrinkage amount due to primary austenite (vol. %)
Eeg=Amount of expansion due to eutectic graphite crystallization (vol. %)
Se γ=Shrinkage amount due to eutectic austenite crystallization (vol. %)

Here, Epg is used when the chemical composition is a hypereutectic composition, and Spγ is used when the chemical composition is a hypoeutectic composition. Each item is obtained by the following equations (2), (3), (4), (5), and (6).

$$Sl = (Ti - 1150)/100 \times 1.5 \qquad (2)$$

$$Epg = (Cx - Ce)/(100 - Ce) \times 3.4 \times 100 \qquad (3)$$

$$Sp\gamma = (Ce - Cx)/(Ce - C\gamma) \times -3.5 \qquad (4)$$

$$Eeg = [(1-Sl)/100] \times [(100-Cx)/(100-Ce)] \times [(Ce-C\gamma)/(100-C\gamma)] \times 3.4 \times 100 \qquad (5)$$

$$Se\gamma = [(1-Sl)/100] \times [(100-Cx)/(100-Ce)] \times [(100-Ce)/(100-C\gamma)] \times -3.5 \qquad (6)$$

Ti=Initial temperature in a mold (° C.)
Ce=Amount of carbon at eutectic point (mass %)
Cx=Amount of carbon in molten metal (mass %)
Cγ=Amount of solute carbon in austenite (mass %)
The amount of liquid shrinkage here is 1.5 vol. % per 100° C. Further, Ce and Cγ are obtained by the following equations (7) and (8).

$$Ce = 4.27 - Si/3 \qquad (7)$$

$$C\gamma = (2.045 - 0.178) \times Si \qquad (8)$$

Si=Amount of silicon in molten metal (mass %)
Finally, the expansion/shrinkage degree was calculated by dividing the obtained expansion/shrinkage amount at each reaction by the respective solid phase ratios. The actual calculation results are shown in section 3.

The input values of the expansion/shrinkage behavior were input as numerical values into the method described in the Non-Patent Document 16, and analyzed. In order to completely reproduce the expansion/shrinkage behavior in the analysis, the solid phase ratio at flow limit was set to 1.0. At the time of calculation, elements smaller than the solid phase ratio at flow limit are considered to be in the same group, and expansion/shrinkage during solidification occurs at the top of the group.

Table 1 shows the physical property values and boundary conditions used for solidification analysis. For these physical property values and boundary conditions, initial values of analysis software and general values were selected. In addition, the division mesh size in the three-dimensional model was uniformly 5 mm.

TABLE 1

Physical properties and heat transfer parameters for test block.

| | Casting | Mold | Chill | Sleeve |
|---|---|---|---|---|
| Density (kg/m³) | 7000 | 1550 | 7850 | 650 |
| Specific heat (kJ/(kg · K)) | 1.047 | 1.047 | 0.670 | 0.921 |
| Thermal conductivity (W/(m · K)) | 20.93 | 1.05 | 33.49 | 0.46 |
| Latent heat kJ/kg) | 209 | — | — | — |
| Heat transfer coefficient (W/(m² · K)) | Casting/Mold: 4186.2 Casting/Chiller: 1395.4 Casting/Sleeve: 837.2 Mold/Chiller: 8372.4 Mold/Sleeve: 837.2 | | | |

(Preparation of Test Materials for Shrinkage Cavities Confirmation and Temperature Measurement)

Figure 2:
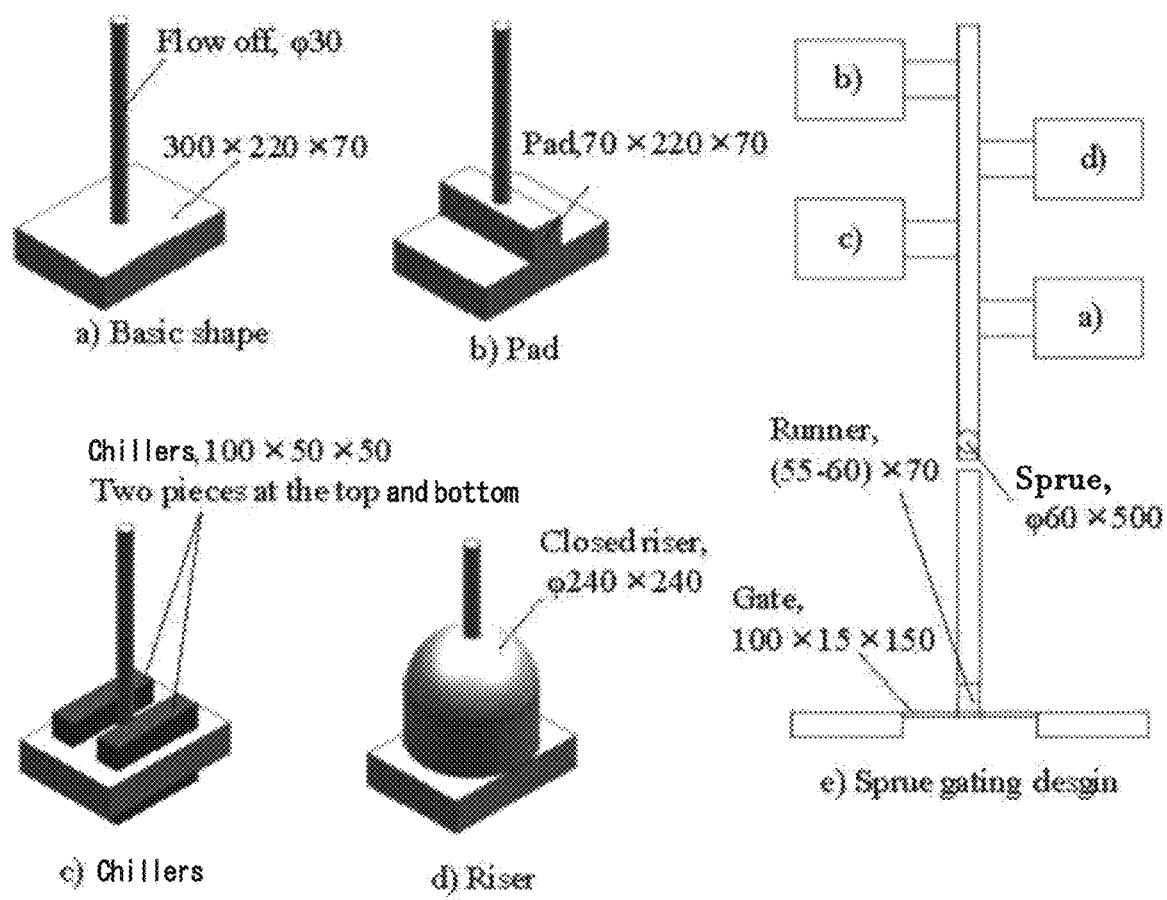
FIG. 2 shows a conceptual perspective view indicating a test block casting design.

It is known that various factors besides coagulation characteristics are involved in the generation of shrinkage cavities. In the present investigation, four kinds of plate test materials were actually cast in order to eliminate such disturbances and confirm the tendency of shrinkage cavities under large-sized SGI production conditions. FIG. 2 shows the shape of the test materials and the casting design. The test materials were based on a riserless design of extension scale 8/1000, width 220×depth 300×thickness 70 (mm). A pad design was to set a pad of width 220×depth 70×thickness 70 (mm) at the center of the upper mold in the longitudinal direction. A chiller design was to set two pieces of chillers having a width of 50×a depth of 100×a thickness of 50 (mm) in each of the upper and lower molds. A riser design was to set a neck-down riser with a diameter of 240 and a height of 240 (mm). A flow off was φ30 (mm), and was set at one place in the center of the upper surface of each test material.

In addition, in order to minimize differences in casting conditions such as chemical composition and casting temperature, a mold was produced by connecting four types of the test materials to a runner in a single molding flask. The mold was kneaded with silica sand at a ratio of 0.8 wt % of a furan resin and a curing agent at a ratio of 40 wt % (based on resin), and the mold strength was aimed at 4.5 MPa or more so as not to move the mold wall. Alcohol-based MgO-based mold wash was used, and after ignition drying, natural drying was performed for 24 hours or more so that the mold strength was sufficiently restored.

Figure 3:
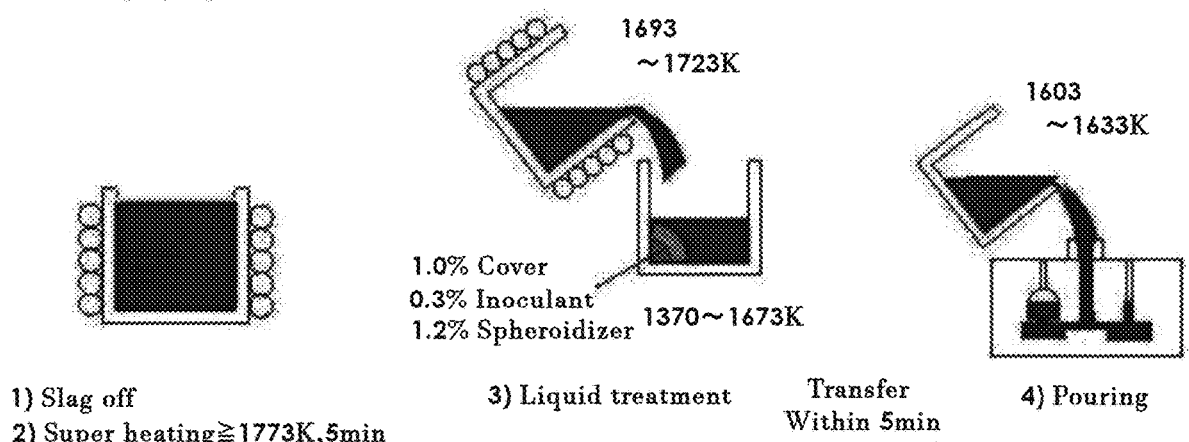
FIG. 3 shows a conceptual perspective view indicating melting and casting procedures.

The melting and casting methods are shown in FIG. 3. Melting was performed using a low-frequency induction furnace, and product returned materials were used as molten materials. After the melting, when the temperature reached 1723K, the components were adjusted, superheated at 1770K or more for 5 minutes, and then the temperature was cooled down naturally and the molten metal was discharged. 1.2% by weight of Fe-45% Si-5.8% Mg alloy, 0.3% by weight of Fe-50% Si alloy and 1.0% by weight of cover material in a ladle were successively placed, and spheroidized by sandwich method and inoculation were performed. The casting was performed within 5 minutes from the end of the reaction to the completion of the casting, and the chemical component analysis after the spheroidizing was performed by an emission spectrometer.

A chemical composition target was a hypoeutectic component, and a volume balance was adjusted to be positive by a completion of solidification from the theoretical volume change. In addition, for the measurement of cooling curve, another identical mold, in which a K-type thermocouple was installed at the center of the plate thickness of each test material, was produced, and casting was continued. Cooling in the mold is performed until the temperature measurement position is 100° C. or less, sand was removed with a shot blasting machine after removing the molding flask, the gate and the flow off were separated by a gas cutting, and the gas cutting surface was ground with a grinder so as to be smooth.

(Experimental Results and Consideration)

Casting Results of the Test Materials (1) Casting Results

Melting, spheroidizing and casting could be performed without any problems. Table 2 shows the results of casting from actual melting, and Table 3 shows the chemical composition. From the table, it can be seen that casting was performed with a composition equivalent to FCD450 (JIS G 5502), and the yield of Mg was good.

TABLE 2

Result of melting, liquid treatment and pouring.

| | | Tapping | After the magnesium reaction has finished to pouring | Pouring |
|---|---|---|---|---|
| Schedule | | 1708 ± 15K | up to 500 | 1618 ± 15K |
| Test block Result | for thermal analysis | 1700K | 2'15 | 1617K, 32 sec |
| | for shrinkage check | | 3'13 | 1604° C., 33 sec |

TABLE 3

Chemical composition of test blocks. (mass %)

| C | Si | Mn | P | S | Ce | Mg | CE |
|---|---|---|---|---|---|---|---|
| 3.31 | 2.38 | 0.30 | 0.06 | 0.011 | 0.00 | 0.059 | 4.10 |

Figure 4:
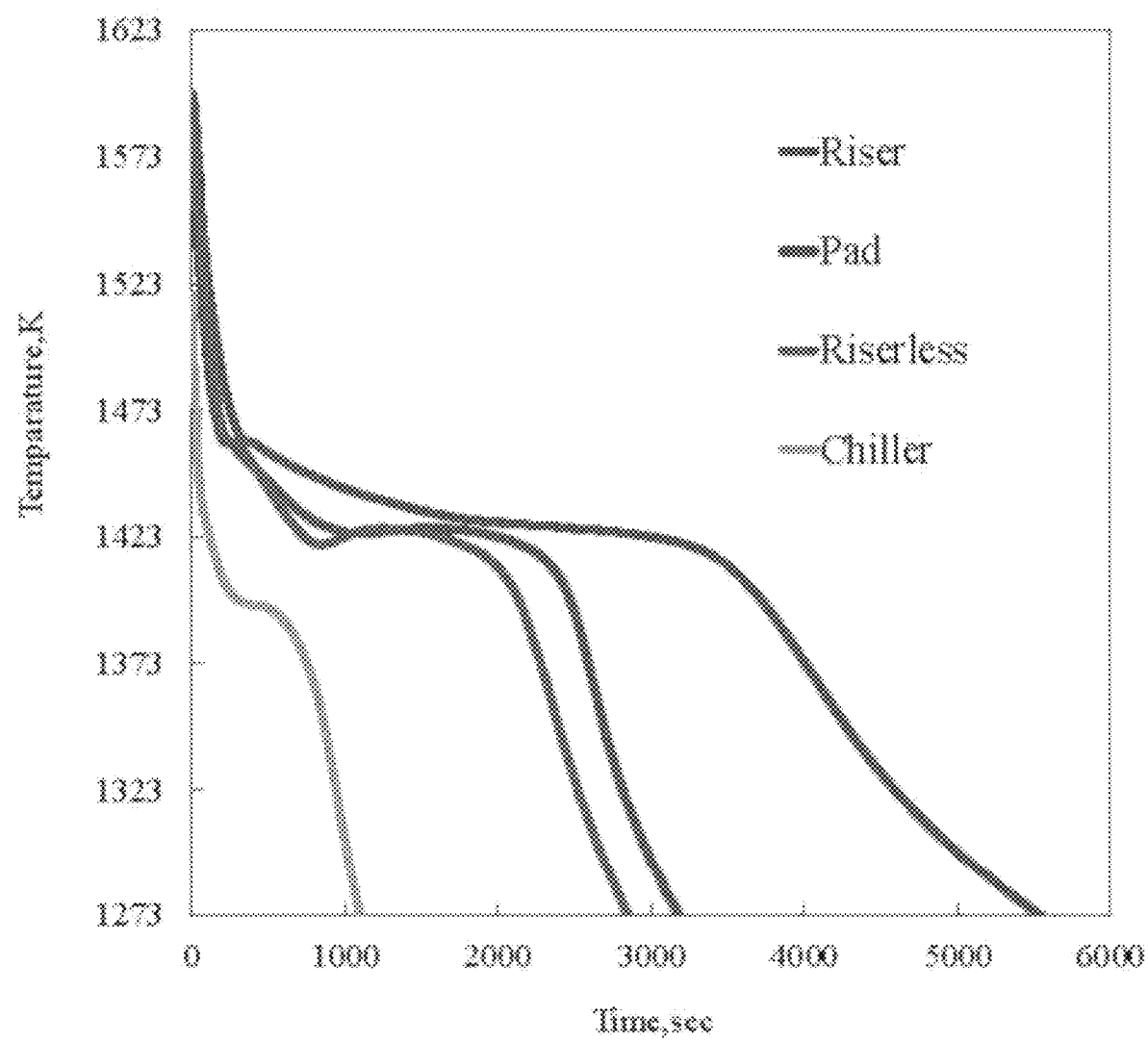
FIG. 4 shows a graph indicating cooling curve for each casting method.

FIG. 4 shows the cooling curves for each casting method. The eutectic temperature were higher and the solidification completion time were longer in the order of the chiller method, the riserless method, the pad method and the riser method, and it can be seen that the temperature measurement was performed without any problems.

TABLE 4

Theoretical volumetric change of test blocks.

| | Casting Design | Liquid Contractraction | Primary crystalization | Contraction of eutectic austenite | Expansion of eutectic graphite | Volume change from Pouring to completion of Solidification |
|---|---|---|---|---|---|---|
| 1 | Chillers | −1.37 | −0.27 | −3.39 | 6.43 | 1.40 |
| 2 | Riserless | −2.48 | −0.27 | −3.35 | 6.35 | 0.25 |
| 3 | Pad | −2.28 | −0.27 | −3.36 | 6.37 | 1.40 |
| 4 | Riser | −2.63 | −0.27 | −3.35 | 6.34 | 0.09 |

(2) Calculation of Expansion/Shrinkage Behavior

Figure 5:
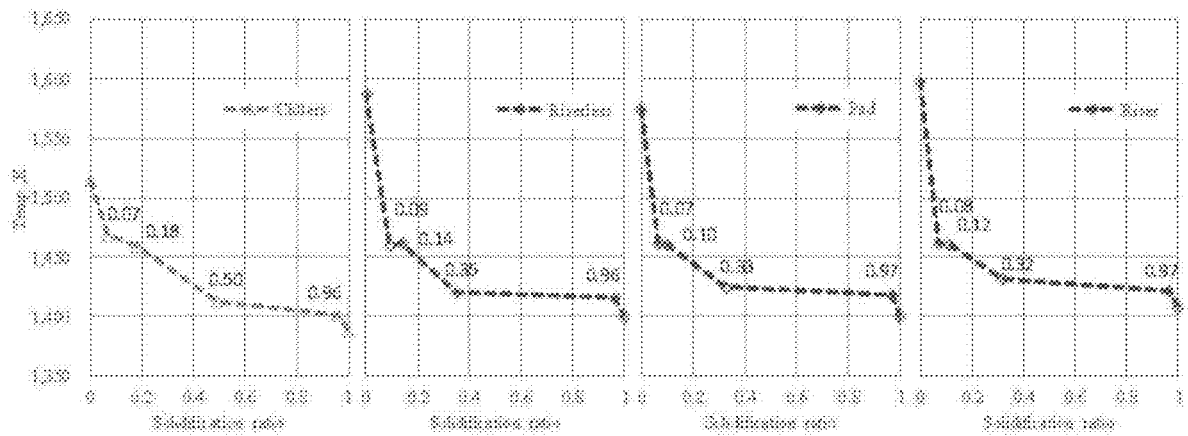
FIG. 5 shows a graph indicating a relationship between a temperature at the time of each reaction until the completion of solidification calculated from measured cooling curve, and solid phase ratio.

FIG. 5 shows the relationship between the temperature during each reaction and the solid phase ratio up to the completion of solidification determined from the measured cooling curve. The correlation between the length of solidification completion time of each test material and the solid phase ratio of each reaction can be confirmed in the eutectic reaction zone, and the austenite shrinkage zone, which occurs between cells and at the end of solidification. As the solidification completion time becomes longer, the eutectic reaction section tends to be longer and the intercellular austenite shrinkage section tends to be shorter.

Next, theoretical volume changes are shown in Table 4. Because the test materials were cast with the same molten metal, the chemical compositions were all the same. Because the initial temperatures of the molten metal in the mold at the time of completion of casting were different, they were read from the measured cooling curve and each was calculated. From the table, it can be seen that the volume balance of all the test materials is positive until the solidification is completed, and that the chemical composition is theoretically such that shrinkage cavities do not occur even in the riserless method.

Figure 6:
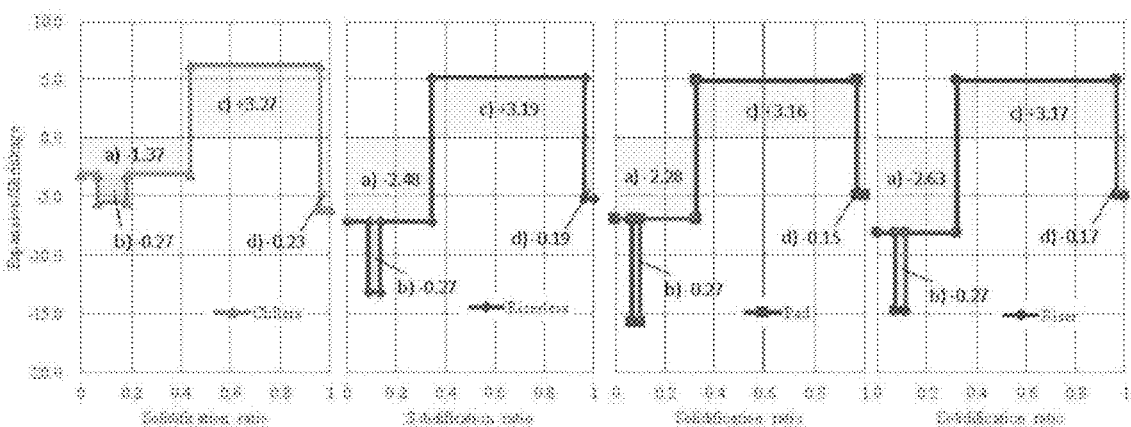
FIG. 6 shows a graph indicating expansion/shrinkage behavior until the solidification is completed.

FIG. 6 shows the expansion/shrinkage behavior until the solidification is completed. The expansion/shrinkage degree was calculated by dividing the calculated theoretical volume change at each reaction by the solid phase ratio. When the expansion/shrinkage degree of each test material having different coagulation completion times during the reaction is confirmed, the longer the coagulation completion time, the smaller the degree of shrinkage of intercellular austenite generated at the end of the solidification.

(3) Analysis Results of the Shrinkage Cavities

Figure 7:
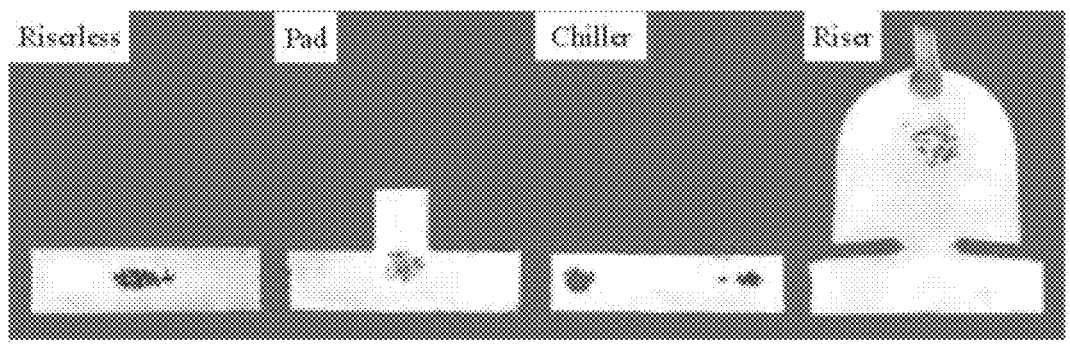
FIG. 7 shows a figure indicating penetrant testing results of center cross section of test material produced by each casting method.
Figure 7:
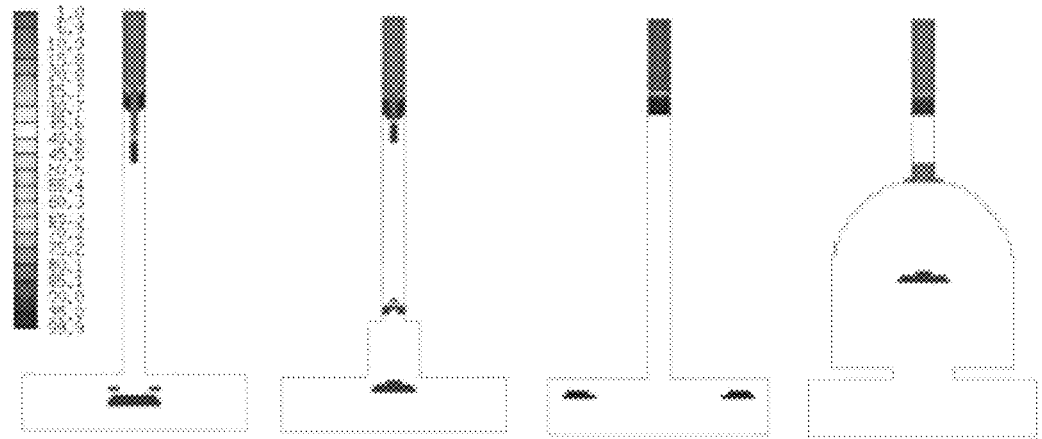
Figure 7:
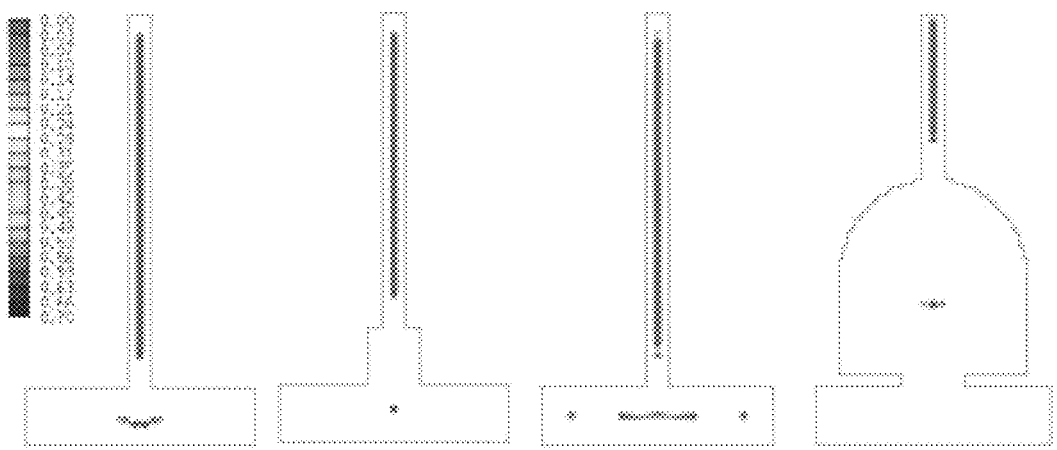

FIG. 7 shows the results of a penetrant inspection test of the center cross section of the test material created by each casting method. In the riserless method, there are indication patterns near the center of the thick part, and the shrinkage cavities are generated. In the pad method, there are indication patterns near the center of the thick part, and the shrinkage cavities are generated. In the chiller method, there are indication patterns near the center of the thick parts at both ends, and the shrinkage cavities are generated. The shrinkage cavities area is larger on the weir side. In the riser method, there is no indication patterns on the flat plate part, but indication patterns can be confirmed inside the riser, and the shrinkage cavities are generated. FIG. 7*b*) shows the analysis results of the present investigation obtained from the expansion/shrinkage behavior, and FIG. 7*c*) shows the results of the G/√R method. Observation locations are the same as the actual shrinkage cavities confirmation cross section. The shrinkage cavities prediction index is expressed as a ratio. The threshold value of the shrinkage cavities is 100% when the solid is completely filled. And, if it is smaller than 100%, it is assumed that the shrinkage cavities are generated, and 99.99% or less is set as the predicted shrinkage cavities generation position. The actual shrinkage cavities generation position and the predicted generation position based on the present analysis result agree well with each other, and it can be seen that it is slightly higher than the prediction by the G/√R method.

The analysis performed in the present example considers expansion/shrinkage during the solidification. In preparing the test materials, we tried to eliminate shrinkage cavities other than solidification such as gas generation and mold wall movement. Therefore, both the test materials and the analysis results can be considered that the cause of shrinkage cavities generation is due to solidification. As the result of confirming the shrinkage cavities of the test materials, the shrinkage cavities were generated at the final solidification position despite the chemical composition having a positive theoretical volume balance. Even in the analysis result, the predicted shrinkage cavities occurrence position shows the same position. And, it is easy to intuitively understand that 99.99% or less of the shrinkage cavities occurrence prediction index is the shrinkage cavities occurrence region, and the reasonable threshold value can be set. Regarding the shrinkage cavities generation area, the shrinkage cavities area of the test material is not equal on the left and right sides in the chiller method. This may be affected by the weir.

However, the tendency of generation is almost the same, and if there is no problem in estimating the shrinkage cavities, it can be said from this analysis result that the position of generation of the shrinkage cavities is more accurate than in the past.

(Application to Large-Sized Thick Material)

Figure 8:
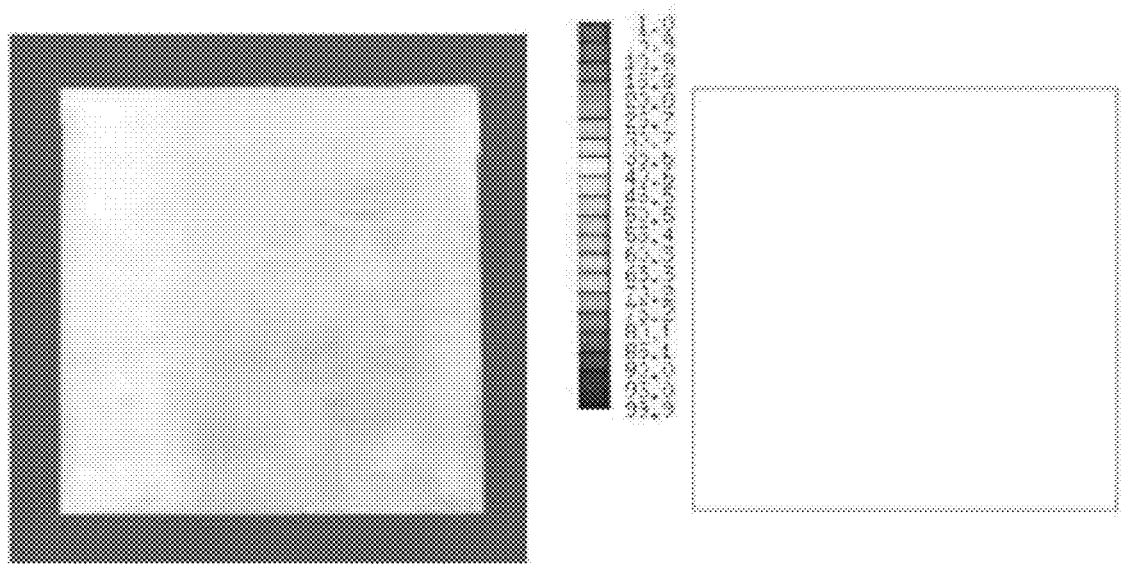
FIG. 8 shows a figure indicating a penetrant testing result of a cross section of center of a 600 mm cube test material.
Figure 9:
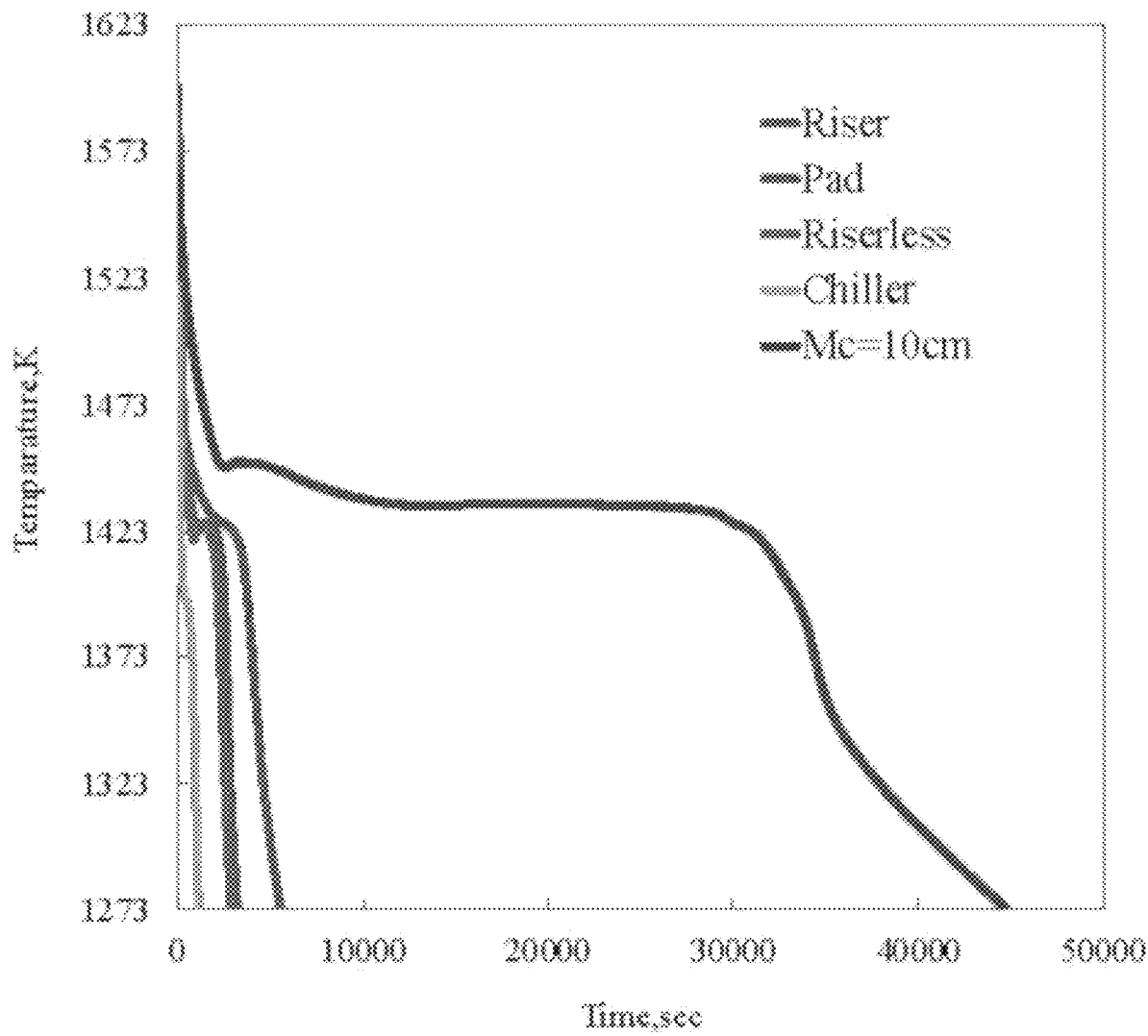
FIG. 9 shows a graph indicating cooling curves of a plate test material and a test material of Mc=10 cm.
Figure 10:
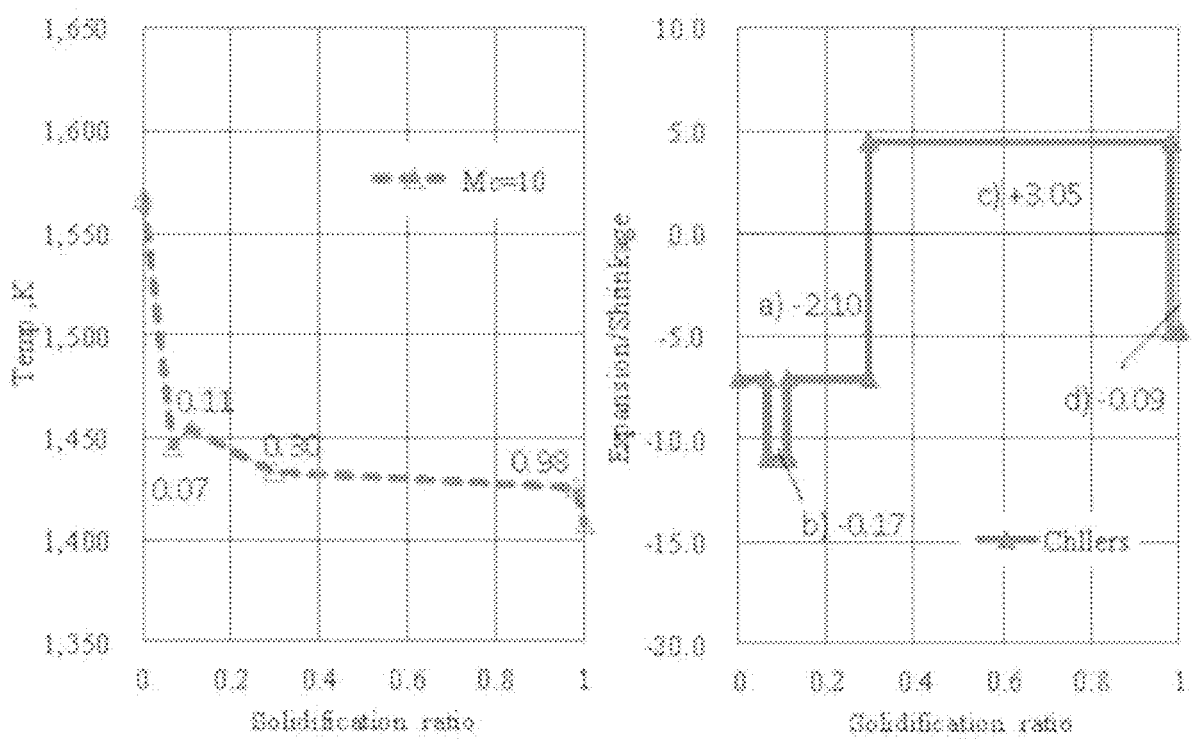
FIG. 10 shows a graph indicating solid phase ratio and expansion/shrinkage amount of the test material of Mc=10 cm.

It is known that the SGI does not have shrinkage cavities when a casting modulus is sufficiently large and a shape is close to a cube. FIG. 8a) shows a result of a penetrant test of a cross section after cutting a center of a 600 mm cubic test material cast at a hypoeutectic composition. Although it has the same hypoeutectic composition as the plate test materials, indication patterns cannot be confirmed at the center. It is considered that the shrinkage cavities does not occur because the eutectic cell of graphite and austenite grows as the solidification time becomes longer to compensate for the shrinkage at the end of solidification. As described above, in order to predict the shrinkage cavities of the thick SGI, it can be seen that, it is necessary to reproduce that no shrinkage cavities occur, in addition to the reproduction of the shrinkage cavities occurrence position. When coagulation analysis of an Mc=10 cm test material is performed by the method of the present investigation, no shrinkage cavities occur at the final solidification position as shown in FIG. 8b). FIG. 9 shows the cooling curves of the plate test materials and the Mc=10 cm test material. The coagulation time of the Mc=10 cm test material is sufficiently long, equal to or more than 9 hours. FIG. 10 shows the solid phase ratio and the expansion/shrinkage amount of the Mc=10 cm test material. A part of the mechanism of shrinkage cavities generation, in which the solidification shrinkage section of austenite between eutectic cells is smaller than plate test material and shrinkage is smaller, is related to the eutectic cell growth during solidification. In such a case, it is considered that the tendency of the occurrence of shrinkage cavities has been reduced in the analysis results, since it is reproduced in the method of the present investigation.

The expansion/shrinkage occurring at the time of solidification were calculated. And, the prediction of the shrinkage cavities performed by using the values of the above expansion and shrinkage, and the casting test results were compared. As a result, the following effects were obtained:

(1) A method, which evaluates the shrinkage cavities based on the expansion/shrinkage behavior calculated from the cooling curve and theoretical volume balance, was developed.

(2) By applying the expansion/shrinkage behavior, the accuracy of the predicted positions of the shrinkage cavities are improved compared to the conventional method.

(3) By considering the amount of the austenite shrinkage between eutectic cells, the existence of the shrinkage cavities agreed well.

(4) It was confirmed that it is useful as a practical shrinkage cavities predictor for the thick and large-sized SGI produced by a Furan self-hardening mold.

In the present invention, a new analytical parameter with a volume balance during solidification of thick spheroidal graphite cast iron was used to predict shrinkage cavities by computer simulation. For more accurate analysis, the cooling curve was divided into several stages according to the several solidification processes. At each stage, an amount of volume change corresponding to a metallographic phase was determined. The result was found to be consistent with the actual shrinkage phenomenon.

As is generally known, shrinkage cavities in ordinary steel castings have been predicted by the computerized hot spot method, cooling gradient method, and Niiyama Criterion.

These methods have been shown to be consistent with the occurrence of shrinkage cavities in casting by skin-forming solidification. However, these results were not consistent with the mushy type of solidification casting such as the spheroidal graphite cast iron. In fact, an article by Eisuke Niiyama does not describe whether the Niiyama Criterion is effective for the spheroidal graphite cast iron.

The formation of the shrinkage cavities in such thick spheroidal graphite cast irons varies and has a specific tendency depending on the shape of the casting.

Solidification of spheroidal graphite cast iron is complex and computerized prediction of shrinkage cavities is not very accurate. Therefore, countermeasures against shrinkage cavities deficiencies at the producing site are based on their experiences.

That is, productivity is deteriorated by adding an extra measurement to the casting. Further, by adding unnecessary steps, producing costs also increase. In the present investigation, experiments, in which shrinkage cavities are predicted from the cooling curve and the theoretical amount of expansion/shrinkage by CAE, are performed.

Experimental Method

In order to quantify the expansion/shrinkage during the solidification, the temperature and the solid phase ratio at each reaction stage from the start to the end of the solidification were measured by a tangent method.

Figure 11:
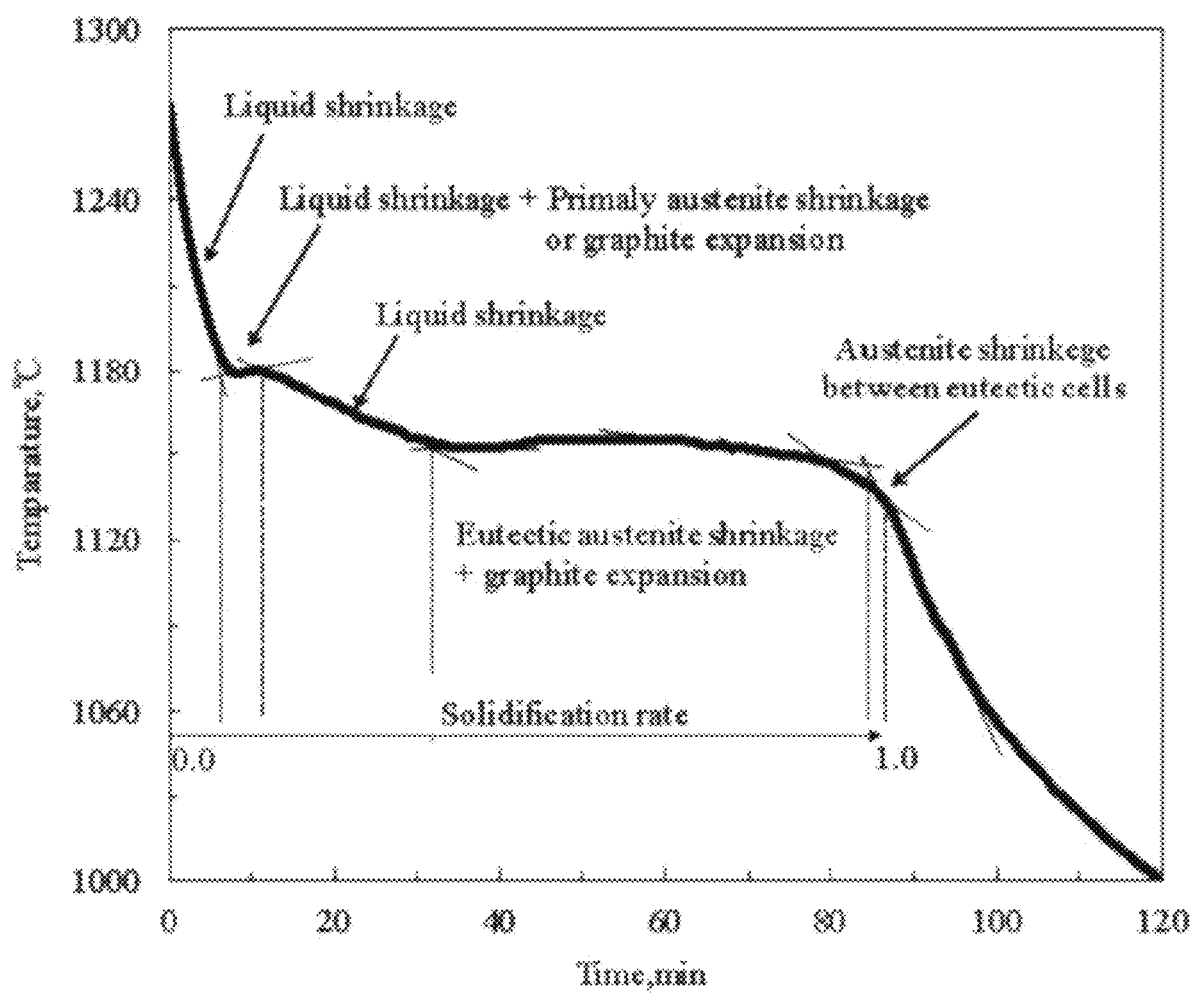
FIG. 11 shows a graph indicating critical points of a volume change in the cooling curve.

FIG. 11 shows the critical points of volume change in the cooling curve. The amount of expansion/shrinkage in each reaction was calculated from the carbon chemical composition, silicon chemical composition, and initial temperature of the test material. The amount of expansion/shrinkage until the end of solidification was calculated using the following equation (1).

$$TV = Sl + Epg (\text{or } Sp\gamma) + Eeg + Se\gamma \quad (1)$$

TV=Amount of volume change (vol. %)
Sl=Amount of liquid shrinkage (vol. %)
Epg=Amount of expansion due to primary graphite (vol. %)
Sp γ=Shrinkage amount due to primary austenite (vol. %)
Eeg=Amount of expansion due to eutectic graphite crystallization (vol. %)
Se γ=Shrinkage amount due to eutectic austenite crystallization (vol. %)

Epg is used when the chemical composition is a hypereutectic composition, and Sp γ is used when the chemical composition is a hypoeutectic composition. Each item is obtained by the following equations (2), (3), (4), (5), and (6).

$$Sl = (Ti - 1150)/100 \times 1.5 \quad (2)$$

$$Epg = (Cx - Ce)/(100 - Ce) \times 3.4 \times 100 \quad (3)$$

$$Sp\gamma = (Ce - Cx)/(Ce - C\gamma) \times -3.5 \quad (4)$$

$$Eeg = [(1-Sl)/100] \times [(100-Cx)/(100-Ce)] \times [(Ce-C\gamma)/(100-C\gamma)] \times 3.4 \times 100 \quad (5)$$

$$Se\gamma = [(1-Sl)/100] \times [(100-Cx)/(100-Ce)] \times [(100-Ce)/(100-C\gamma)] \times -3.5 \quad (6)$$

Ti=Initial temperature in a mold (° C.)
Ce=Amount of carbon at eutectic point (mass %)
Cx=Amount of carbon in molten metal (mass %)
C γ=Amount of solute carbon in austenite (mass %)

The amount of liquid shrinkage here is 1.5 vol. % per 100° C. Ce and Cγ are obtained by the following equations (7) and (8).

$$Ce = 4.27 - Si/3 \quad (7)$$

$$C\gamma = (2.045 - 0.178) \times Si \quad (8)$$

Si=Amount of silicon in molten metal (mass %)

Finally, the expansion/shrinkage degree was calculated by dividing the obtained expansion/shrinkage amount at each reaction by the respective solid phase ratios. As described above, the expansion/shrinkage behavior, which occurs during the solidification, can be quantified. The quantified values were input to the casting simulation software "ADSTEFAN" as the amount of expansion/shrinkage.

Experimental Results and Consideration

Figure 12:
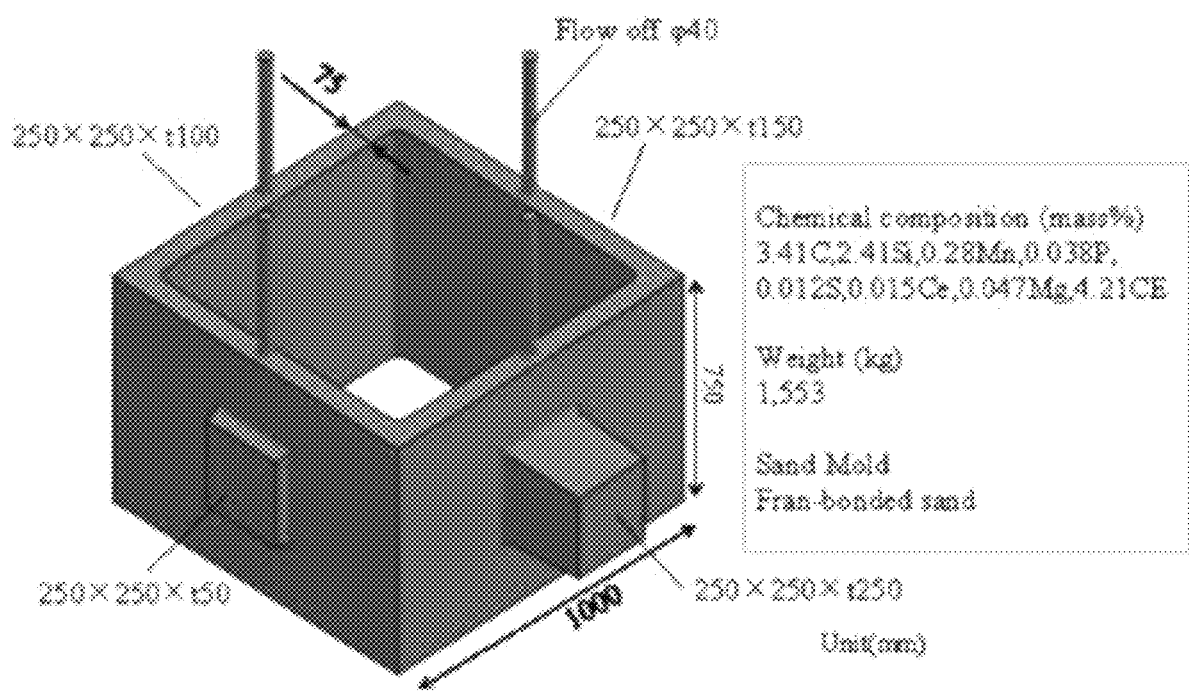
FIG. 12 shows a three-dimensional view indicating a shape of the test material used for confirming the effect of the present invention.

FIG. 12 shows a shape of a test material. The test material has a rectangular prism cavity surrounded by walls of 1000 mm length, 650 mm height and 75 mm thickness on each side, and each wall has a protrusion of different thickness.

Figure 13:
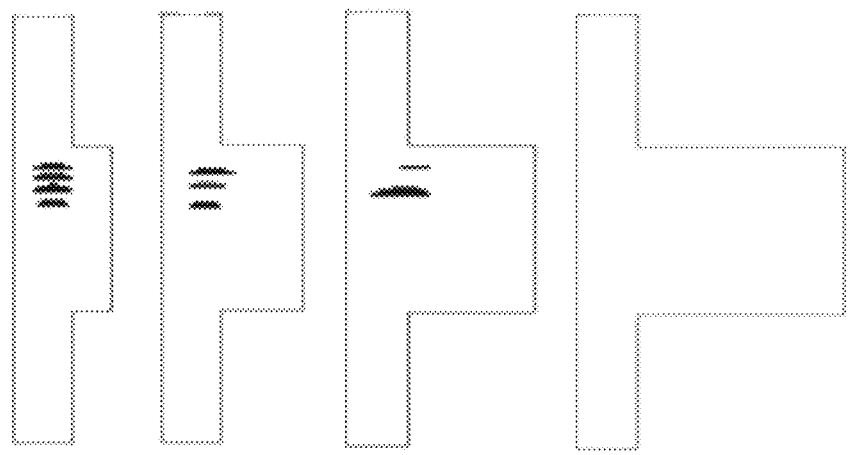
FIG. 13 shows a figure indicating an analysis result for explaining the effect of the present invention.
Figure 13:
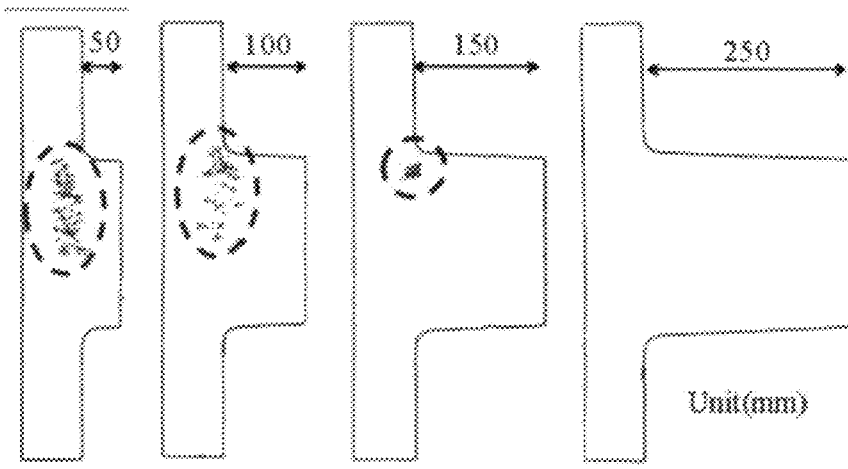
Figure 13:
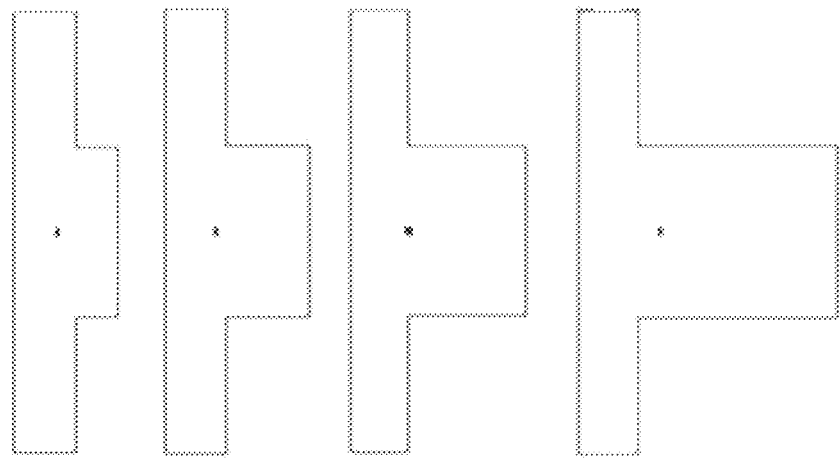

FIG. 13 shows the analysis results. The shrinkage cavities generation standard was set to 99.9% or less. No shrinkage cavities appeared apparently in the case of a 250 mm thick protrusion.

On the other hand, as shown in FIG. 13(1), shrinkage cavities appeared in the case of the protrusion having the thickness other than 250 mm. And, the location of this shrinkage cavities was not the location where it finally solidifies.

In order to confirm the above, it was also measured by a transfer method. As shown in FIG. 13(2), the shrinkage cavities were observed. These were almost the same result as FIG. 13(1). On the other hand, in the case of Niiyama Criterion, shrinkage cavities occur at the final solidification position as shown in FIG. 13(3), which is different from the result of the test material shown in FIG. 13(2).

The shrinkage prediction was performed by connecting the cooling curve and the theoretical volume balance. We have confirmed that the new method, which can analyze more accurately than the current situation, can be provided.

In general, the expansion/shrinkage behavior is determined as follows. The theoretical volume of shrinkage/expansion are determined by follows.

1. Chemical composition and filling completion temperature
2. Solidification cooling curve In the above-described invention, the following method was used. The theoretical volume of shrinkage/expansion associated with solidification are calculated, and the volumes are numerically substituted to the zones, which are separated by the inflection points of the cooling curve, and are applied.

However, depending on the product shape, the apparent expansion/shrinkage may differ from the actual expansion/shrinkage.

Therefore, solidification analysis with higher accuracy can be achieved by considering the apparent expansion/shrinkage behavior.

Figure 14:
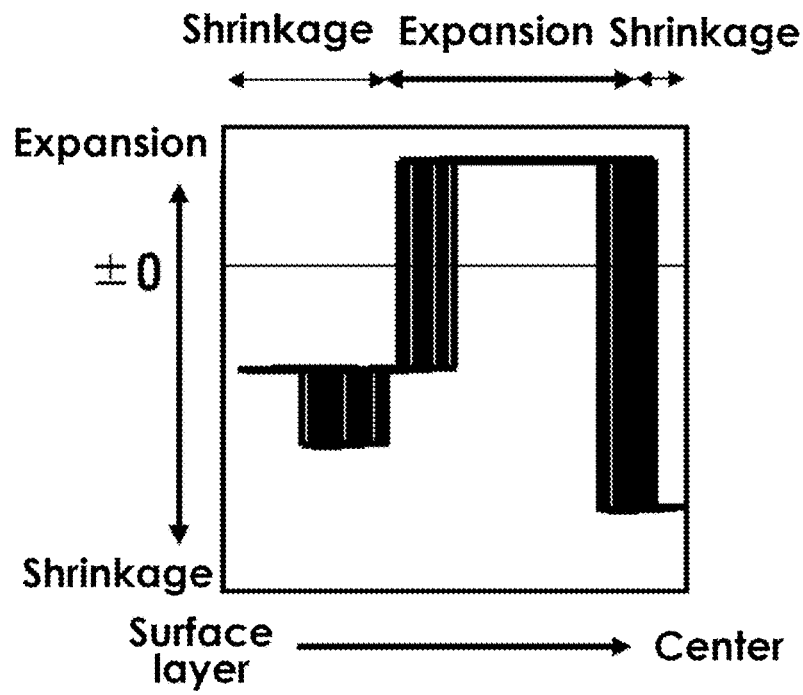
FIG. 14 shows a figure indicating an apparent expansion/shrinkage behavior.
Figure 14:
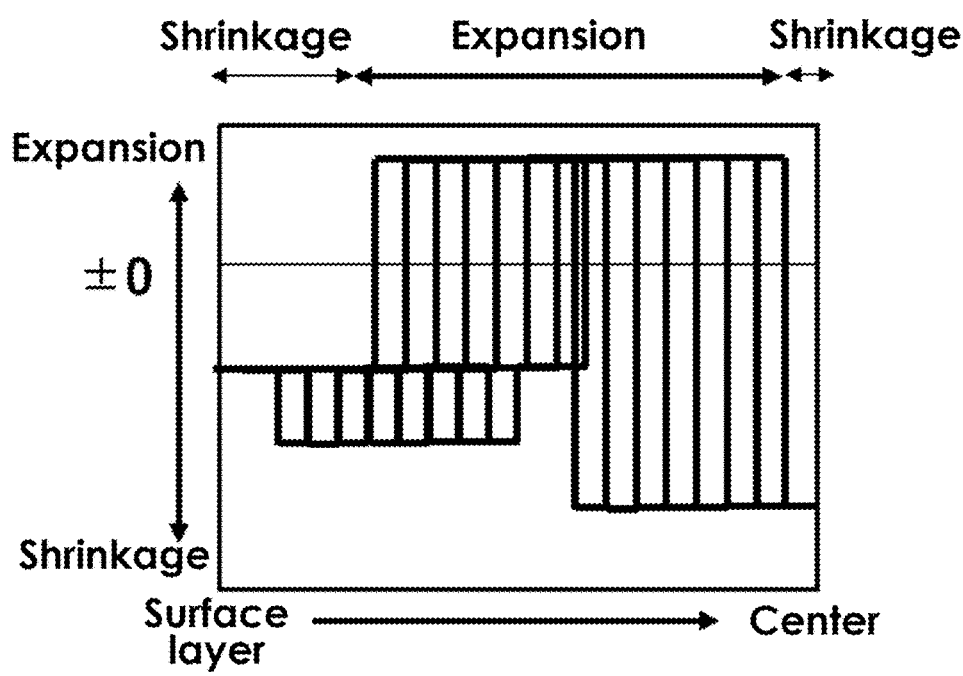

It is described with reference to FIG. 14. The chain of expansion/shrinkage, which occurs during solidification is considered the "apparent" expansion/shrinkage behavior.

This is for expressing a temporal change from the solidification form observed during the solidification. In the small-sized SGI, the surface layer and the center solidify at the almost same time (FIG. 14(a)) while undergoing a mushy-type solidification, whereas the large-sized SGI solidifies from the surface layer toward the center while undergoing a mushy-type solidification (FIG. 14(b))". In this case, the shrinkage occurrence in the early stage of coagulation and the expansion occurrence timing are apparently advanced, and the expansion completion timing is apparently delayed, so that the shrinkage generation timing in the end of the solidification is also delayed.

Therefore, the apparent expansion/shrinkage behavior is considered as follows.

Figure 15:
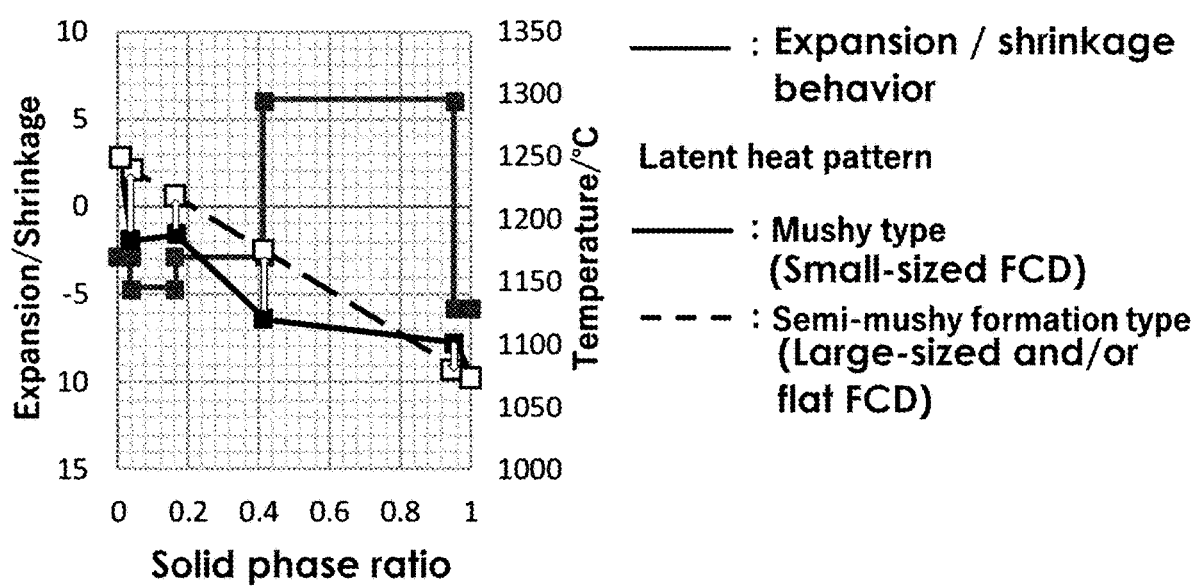
FIG. 15 shows a figure showing a method of correcting an apparent expansion/shrinkage behavior.

As shown in FIG. 15, a latent heat pattern released during solidification is connected to a straight line from solid phase ratio 0 to 1.0 (or 0.999 for convenience). As a result, the temperature, at which shrinkage occurs at the early stage of solidification, and the temperature, at which expansion occurs, are increased, and the temperature, at which expansion is completed, is reduced.

What is claimed is:

1. A casting metal solidification process, comprising determining an amount of expansion/shrinkage for each solidification step length of said casting metal solidification process separated by inflection points in a cooling curve, wherein said determining comprises:
    a. setting a solid phase ratio at a completion of pouring to 0,
    b. setting a solid phase ratio at an end of solidification to 1.0, and
    c. determining the expansion/shrinkage amount for the each solidification step length by proportionally distributing the each solidification step length to total solidification phase ratio length,
wherein expansion/shrinkage is calculated separately for each of the following casting stages: liquid shrinkage, primary crystal reaction, eutectic reaction, and shrinkage of austenite between eutectic cells,
and wherein said determining enables said metal solidification process to be performed without requiring a riser.

2. The casting solidification method according to claim 1, wherein a cast product is a cast product having a part of 50 mm or more in thickness.

3. The casting solidification method according to claim 1, wherein the casting is a spheroidal graphite cast iron casting.

4. A casting metal solidification process according to claim 1, further comprising a step of obtaining a straight line by connecting a point of said solid phase ratio at a completion of pouring and a point of said solid phase ratio at an end of solidification after a step of said setting a solid phase ratio at an end of solidification to 1.0.

5. An electronic program, comprising: (a) a step of determining (i) inflection points from a cooling curve of a casting solidification method and (ii) each solidification step length separated by the inflection points; and (b) a step of setting to 0 a solid phase ratio at a completion of pouring, setting to 1.0 a solid phase ratio at an end of solidification, and determining an expansion/shrinkage amount for the each solidification step length by proportionally distributing the each solidification step length to total solidification phase ratio length, wherein expansion/shrinkage is calculated separately for each of the following casting stages: liquid shrinkage, primary crystal reaction, eutectic reaction, and shrinkage of austenite between eutectic cells,
    and wherein said electronic program enables said casting solidification method to be performed without requiring a riser.

* * * * *